United States Patent [19]
Hardtmann

[11] 4,119,720
[45] Oct. 10, 1978

[54] UNSATURATED ESTERS OF 4-HYDROXY-2-QUINOLINONE-3-CARBOXYLIC ACIDS AND SALTS THEREOF

[75] Inventor: Goetz E. Hardtmann, Morristown, N.J.

[73] Assignee: Sandoz, Inc., E. Hanover, N.J.

[21] Appl. No.: 813,267

[22] Filed: Jul. 6, 1977

[51] Int. Cl.² .................... A61K 31/47; G07D 215/22
[52] U.S. Cl. ............................ 424/258; 260/287 AN; 260/287 K
[58] Field of Search .................. 260/287 AN, 287 K; 424/258

[56] References Cited

U.S. PATENT DOCUMENTS 3,960,868   6/1976   Ferrini et al. .................... 260/287 K

FOREIGN PATENT DOCUMENTS 806,848 10/1973 Belgium.

Primary Examiner—Donald G. Daus
Assistant Examiner—David E. Wheeler
Attorney, Agent, or Firm—Gerald D. Sharkin; Richard E. Vila

[57] ABSTRACT

Disclosed are compounds which are unsaturated esters of 4-hydroxy-2-quinolinone-3-carboxylic acids, e.g., 1-allyl-6,7-dimethoxy-4-hydroxy-2-quinolinone-3-carboxylic acid allyl ester, useful as anti-allergic agents, and prepared by reacting an isatoic anhydride with an alkali metal salt of a malonic acid unsaturated ester.

78 Claims, No Drawings

UNSATURATED ESTERS OF 4-HYDROXY-2-QUINOLINONE-3-CARBOXYLIC ACIDS AND SALTS THEREOF

DISCLOSURE OF THE INVENTION

The present invention relates to chemical compounds and their use as pharmaceutical agents, and more particularly to compounds which are 4-hydroxy-2-quinolinone-3-carboxylic acid unsaturated esters which are useful as anti-allergic agents.

The compounds of the present invention may be represented by the structural formula I:

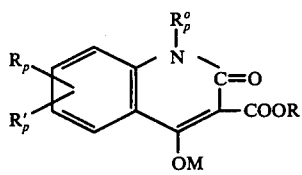

wherein $R_p^o$ is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

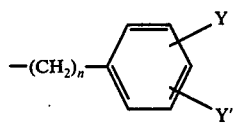

$n$ is 0 or 1,

M is hydrogen or a pharmaceutically acceptable cation,

R is alkenyl of 3 to 6 carbon atoms or alkynyl of 3 to 6 carbon atoms,

Y and Y' are independently hydrogen, halo of atomic weight of from 18 to 80, i.e., fluoro, chloro or bromo, alkyl of 1 to 3 carbon atoms, alkoxy of 1 to 3 carbon atoms, trifluoromethyl or nitro, with the proviso that only one of Y and Y' can be from the group consisting of nitro and trifluoromethyl, and $R_p$ and $R_p'$ are independently hydrogen, halo of atomic weight of from 18 to 80, i.e., fluoro, chloro or bromo, alkyl of 1 to 4 carbon atoms, alkoxy of 1 to 4 carbon atoms, nitro or trifluoromethyl, or $R_p$ and $R_p'$ together form 6,7-methylenedioxy, with the proviso that only one of $R_p$ and $R_p'$ can be from the group consisting of nitro and trifluoromethyl, with the further proviso that the unsaturation in any alkenyl or alkynyl is on other than the alpha carbon atom.

The compounds of the formula I may be conveniently prepared by reacting a compound of the formula II:

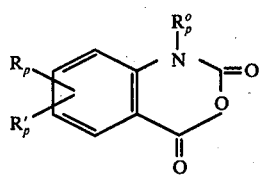

in which $R_p^o$, and $R_p$ and $R_p'$ are as defined above, with a compound of formula III:

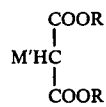

in which R is as defined above, and M' signifies an alkali metal.

The process is suitably carried out in an inert organic solvent, e.g., dimethylacetamide, and at a temperature of from 0° C. to 150° C., preferably 60° C. to 120° C. followed, if necessary or desired, by neutral or acid hydrolysis to obtain the desired compound I from any 4-alkali metal salt thereof initially produced.

The compounds of formula III may be produced from the corresponding dialkenyl or dialkynyl malonates by reaction with a strong alkali metal base, e.g., sodium hydride, and in an inert organic solvent, e.g., dimethylacetamide.

The compounds I in which M is a pharmaceutically acceptable cation, e.g., sodium, potassium, ammonium, tetraalkylammonium, etc., may be also and preferably prepared from the compound I in which M is hydrogen by procedures well known in the art, e.g., by treating with a base having such pharmaceutically acceptable cation, such as dilute aqueous sodium hydroxide, in a water miscible solvent.

The resulting compounds of formula I may be isolated and purified using conventional techniques.

The compounds of the formulae II and III employed in the preparation of compound I are either known or may be produced in conventional manner from know materials.

The compound 4-methoxy-2-quinolinone-3-carboxylic acid ethyl ester is known from McCorkindale, Tetrahedron, 1961, Vol. 14, pp. 223–229, but to my knowledge has not been associated with any useful pharmacological activity. Also, Coutts et al., J. Chem. Soc. 1962, 2518–21, disclose the compound 4-hydroxy-2-quinolinone-3-carboxylic acid ethyl ester, but without the association of any useful pharmacological activity. Similarly, Brown, Australian J. Chem. 8, 121–4 (1955), disclose various N-unsubstituted-polyalkoxy-4-hydroxy-2-quinolinone-3-carboxylic acid esters, e.g., 6,7-dimethoxy-4-hydroxy-2-quinolinone-carboxylic acid methyl ester.

Compounds I of particular interest as anti-allergic agents include those in which $R_p$ nd $R_p'$ are other than 6,7-methylenedioxy and $R_p^o$ is: (a) alkenyl of 3 to 6 carbon atoms; (b) alkynyl of 3 to 6 carbon atoms; (c) cycloalkyl of 3 to 6 carbon atoms; (d) cycloalkylalkyl in which the cycloalkyl portion is of 3 to 6 carbon atoms and the alkyl portion is 1 or 2 carbon atoms; (e) alkyl of 1 to 6 carbon atoms; and (f) Y,Y'-substituted benzyl wherein Y and Y' are as above defined. In the subgrouping of compounds of the formula I in which $R_p^o$ is hydrogen, it is generally preferred that $R_p$ is hydrogen, fluoro, chloro, bromo, alkyl of 1 to 4 carbon atoms or alkoxy of 1 to 4 carbon atoms and $R_p'$ is fluoro, chloro, bromo, alkyl of 1 to 4 carbon atoms or alkoxy of 1 to 4 carbon atoms. In the subgrouping of compounds I in which $R_p$ and $R_p'$ are other than 6,7-methylenedioxy it is generally preferred that $R_p$ and $R_p'$ are independently hydrogen, fluoro, chloro, bromo, alkyl of 1 to 4 carbon atoms or alkoxy of 1 to 4 carbon atoms.

Particularly preferred compounds I with $R_p$ and $R_p'$ being other than methylenedioxy are those having one or more, preferably all three, of the following features: (a) $R_p^o$ being alkyl or alkenyl, more preferably alkenyl, most preferably allyl; (b) $R_p$ and $R_p'$ both being alkoxy, more preferably representing 6,7-dialkoxy, most preferably 6,7-dimethoxy; (c) R being alkenyl, more preferably allyl; and (d) the compounds in which M is hydrogen.

In the subgrouping of compounds I in which $R_p$ and $R_p'$ together form 6,7-methylenedioxy, the preferred significances of $R_p^o$ in such compounds are alkyl and alkenyl, more preferably alkenyl, and most preferably allyl; such compounds preferably being in free acid form (i.e., M being hydrogen).

The compounds of formula I (in free acid or salt form) are useful because they possess pharmacological activity in animals. In particular they possess disodium chromoglycate (DSCG)-like activity, in particular histamine release inhibiting activity, and are therefore useful in the treatment of allergic conditions, such as allergic asthma, as indicated in the passive cutaneous anaphylaxis test in the rat. Female rats (180-200 g) are sensitised by subcutaneous administration of 1 mg of egg albumin (Merck Nr. 967) and 200 mg. of Al(OH)$_3$ dissolved in 1 ml of physiological saline and 0.5 ml of Haemophiluspertussis vaccine (Schweizerisches Serum and Impfinstitut, Bern; Nr. 115 325; $4 \times 10^{10}$ organism/ml) intraperitoneally. Fourteen days later, the animals are exsanguinated, the blood centrifuged, the serum collected and deep frozen. The serum thus obtained (anti-serum) is injected intradermally (0.1 ml of a 1:200 diluted serum per injection site) at four sites on the backs of untreated, female rats. Twenty-four hours later each rat is administered 0.1 to 5.6 mg/kg i.v. or 0.1 to 100 mg/kg p.o. of the test compound, and either immediately or 5 or 30 minutes afterwards, in the case of intravenous administration, or 15 or 60 minutes afterwards, in the case of oral administration, afterwards egg albumin (5 mg/ml i.v.) dissolved in physiological saline containing 0.25% Evans Blue dye (Merck Nr. 3169). The egg albumin elicits a cutaneous anaphylactic reaction, the intensity of which is proportional to the extent to which the Evans Blue dye diffuses into the tissue surrounding each of the four sensitisation sites. Thirty minutes after the administration of the egg albumin, the rats are killed with ether, the underside of the skin of the back of each animal is exposed and the diameter of the areas of blue dye surrounding each of the four sensitisation sites are measured. Each dose of test compound is investigated in between four and six rats and the mean diameter compared with the mean value obtained in four solvent-treated control rats. The percentage inhibition is taken as the percentage of the mean diameter in the test animals relative to the mean diameter in the controls.

The DSCG-like activity, in particular histamine release inhibiting activity, can be confirmed by inhibition of histamine release in the rat peritoneal mast cell test, basically as described by Kusner et al., J. Pharmacol. Exp. Therap. 184, 41-46 (1973), with the following modification: after sedimentation of the mast cells by centrifugation at 350 $\times$ g and 4° C., the sediments are taken up in 1 ml of Hank's balanced salt solution (HBSS) (buffered to a pH of 6.9) and pooled. The resulting suspension is centrifuged, washed again with HBSS and sedimented. The thus purified mast cells are prepared as 2 ml suspensions in HBSS. To these are added either 2 ml of HBSS, to determine the spontaneous histamine release, or 2 ml of HBSS and 2.24 ug of compound 48/80 (N-methylhomoanisylamineformaldehyde condensate; a histamine liberato from Burroughs Wellcome and Co. Inc., Tuckahoe, N.Y. USA), to determine the 48/80 induced histamine release, or 2 ml of HBSS with 2.24 ug of 48/80 and from 18 to 180 ug/ml of the test compound, to determine the 48/80 induced histamine release in the presence of the test compound.

The 48/80 induced histamine release minus the spontaneous histamine release is taken as 100% histamine release. The 48/80 induced histamine release in the presence of the test compound minus the spontaneous histamine release is then compared with the 100% value to determine the percentage inhibition by the test compound. [The histamine determination is effected in conventional manner, for example, as described in the above-mentioned Kuzner et al. article, or in Kusner and Herzig, Advances in Automated Analysis, 429 (1971)].

For the above-mentioned anti-allergic use, the dosage administered will, of course, vary depending on the compound employed, mode of administration and treatment desired. However, satisfactory results are generally obtained on the administration of compounds I at a daily dosage of from about 0.3 to 100 mg/kg of animal body weight. conveniently given in divided doses two to four times daily, or in sustained release form. For the larger mammals, the total daily dosage is in the range from about 20 to 800 mg of the compound admixed with a solid or liquid pharmaceutical carrier, of conventional type, and divided dosage forms comprise 5 to 400 milligrams of the compound in admixture with a solid or liquid pharmaceutical carrier. As will be appreciated, the treatment of allergic conditions according to the invention is based on histamine release inhibition activity and is therefore essentially symptomatic. The ability to employ such compounds in prophylactic treatment of such allergic conditions (as evident from the DSCG-like activity) is a feature of such compounds. However, the good oral activity relative to DSCG is a further feature.

Pharmaceutical compositions provided by the invention and useful for treating allergic conditions due to histamine release contain a compound of the formula I as active ingredient and one or more conventional pharmaceutically acceptable carriers, and such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositions including applicable unit dosage forms thereof may be prepared according to any method known in the art for the manufacture of pharmaceutical compositions. The compounds may also be administered by inhalation therapy techniques in compositions conventionally prepared and adapted for such procedures. The compositions of the invention adapted for either oral, inhalation or parenteral administration may contain from 1% to 90% by total weight of active ingredient in combination with the carrier, more usually 3% to 70%. The preferred unit dosage forms are the essentially solid forms adapted for oral administration, e.g., tablets or capsules.

A representative formulation for administration 2 to 4 times a day for prophylactic treatment of allergic asthma is a capsule prepared by standard techniques to contain the following:

| Ingredient | Weight (mg) |
|---|---|
| 1-Allyl-6,7-dimethoxy-4-hydroxy-2-quinolinone-3-carboxylic acid allyl ester | 30 |
| Kaolin | 210 |

The following examples are given for purposes of illustration only.

EXAMPLE 1

1-Allyl-6,7-dimethoxy-4-hydroxy-2-quinolinone-3-3-carboxylic acid allyl ester

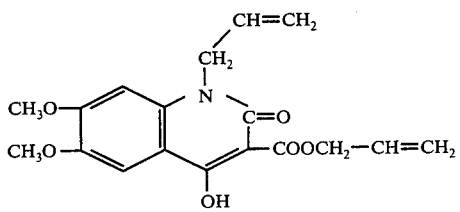

To a solution of 3.0 g. of diallyl malonate in 50 ml. of dimethylacetamide is added portionwise 750 mg. of pentane washed 50% sodium hydride. The resulting solution is stirred at room temperature for 30 minutes and there is then added 4.0 g. of 1-allyl-6,7-dimethoxyisatoic anhydride in 50 ml. of dimethylacetamide. The resulting solution is heated at 120° C. for 3 hours, the dimethylacetamide removed in vacuo, water added, the resulting mixture washed with methylene chloride, acidified with 2 N. hydrochloric acid and extracted with methylene chloride. The organic phase is dried and the methylene chloride exchanged for ether to crystallized and obtain 1-allyl-6,7-dimethoxy-4-hydroxy-2-quinolinone-3-carboxylic acid allyl ester, m.p. 157°–160° C.

EXAMPLE 2

In manner analogous to Example 1, employing appropriate starting materials in approximately equivalent amounts, the following compounds are obtained:

(A) 1-ethyl-4-hydroxy-2-quinolinone-3-carboxylic acid allyl ester.

(B) 1-butyl-7-chloro-4-hydroxy-2-quinolinone-3-carboxylic acid allyl ester.

(C) 1-methyl-6-methoxy-4-hydroxy-2-quinolinone-3-carboxylic acid allyl ester.

(D) 1-methyl-4-hydroxy-2-quinolinone-3-carboxylic acid allyl ester.

(E) 6-methyl-4-hydroxy-2-quinolinone-3-carboxylic acid allyl ester.

(F) 1-allyl-4-hydroxy-2-quinolinone-3-carboxylic acid allyl ester.

(G) 6,7-dimethoxy-4-hydroxy-2-quinolinone-3-carboxylic acid allyl ester.

(H) 1-cyclopentyl-4-hydroxy-2-quinolinone-3-carboxylic acid allyl ester.

(I) 1-propargyl-4-hydroxy-2-quinolinone-3-carboxylic acid allyl ester.

(J) 1-(p-fluorobenzyl)-4-hydroxy-2-quinolinone-3-carboxylic acid allyl ester.

(K) 1-phenyl-4-hydroxy-2-quinolinone-3-carboxylic acid allyl ester.

(L) 1-methyl-6,7-dimethoxy-4-hydroxy-2-quinolinone-3-carboxylic acid allyl ester.

(M) 1-(2-butynyl)-6,7-dimethoxy-4-hydroxy-2-quinolinone-3-carboxylic acid allyl ester.

(N) 1-propyl-6,7-dimethoxy-4-hydroxy-2-quinolinone-3-carboxylic acid allyl ester.

(O) 1-cyclopropylmethyl-6,7-dimethoxy-4-hydroxy-2-quinolinone-3-carboxylic acid allyl ester.

(P) 1-(2-butenyl)-6,7-methoxy-4-hydroxy-2-quinolinone-3-carboxylic acid allyl ester.

(Q) 1-allyl-6,7-methylenedioxy-2-quinolinone-4-hydroxy-3-carboxylic acid allyl ester.

(R) 1-allyl-6,7-dimethoxy-4-hydroxy-2-quinolinone-3-carboxylic acid propargyl ester.

(S) 1-allyl-6-methoxy-7-ethyl-4-hydroxy-2-quinolinone-3-carboxylic acid allyl ester.

(T) 1-allyl-6-methoxy-7-methyl-4-hydroxy-2-quinolinone-3-carboxylic acid allyl ester.

(U) 1-allyl-6,7-dimethyl-4-hydroxy-2-quinolinone-3-carboxylic acid allyl ester.

Another subgrouping of the compounds I of interest as anti-allergic agents are those in which $R_p^o$ is allyl, $R_p$ is alkyl of 1 to 4 carbon atoms in the 7-position, preferably methyl or ethyl, and $R_p'$ is alkoxy of 1 or 2 carbon atoms in the 6-position, preferably methoxy.

What is claimed is:

1. A compound of the formula:

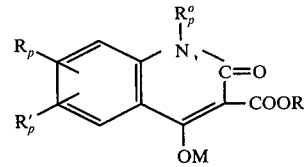

wherein
$R_p^o$ is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

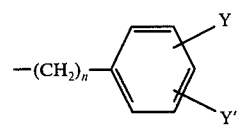

$n$ is 0 or 1,
M is hydrogen or a pharmaceutically acceptable cation,
R is alkenyl of 3 to 6 carbon atoms or alkynyl of 3 to 6 carbon atoms,
Y and Y' are independently hydrogen, fluoro, chloro, bromo, alkyl of 1 to 3 carbon atoms, alkoxy of 1 to 3 carbon atoms, trifluoromethyl or nitro, with the proviso that only one of Y and Y' can be from the group consisting of nitro and trifluoromethyl, and
$R_p$ and $R_p'$ are independently hydrogen, fluoro, chloro, bromo, alkyl of 1 to 4 carbon atoms, alkoxy of 1 to 4 carbon atoms, nitro or trifluoromethyl, or $R_p$ and $R_p'$ together form 6,7-methylenedioxy, with the proviso that only one of $R_p$ and $R_p'$ can be from the group consisting of nitro and trifluoromethyl,
with the further proviso that the unsaturation in any alkenyl or alkynyl is on other than the alpha carbon atom.

2. A compound of claim 1 in which R is alkenyl.

3. A compound of claim 2 in which R is allyl.
4. A compound of claim 1 in which $R_p^o$ is hydrogen.
5. A compound of claim 1 in which $R_p^o$ is alkyl.
6. A compound of claim 1 in which $R_p^o$ is alkynyl.
7. A compound of claim 1 in which $R_p^o$ is cycloalkyl.
8. A compound of claim 1 in which $R_p^o$ is cycloalkylalkyl.
9. A compound of claim 1 in which $R_p^o$ is

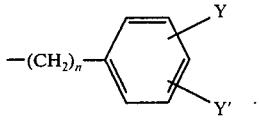

10. A compound of claim 9 in which $n$ is 0.
11. A compound of claim 9 in which $n$ is 1.
12. A compound of claim 1 in which $R_p$ and $R_p'$ are each alkoxy of 1 to 4 carbon atoms.
13. A compound of claim 12 in which $R_p$ and $R_p'$ represent 6,7-dialkoxy.
14. A compound of claim 13 in which $R_p$ and $R_p'$ represent 6,7-dimethoxy.
15. A compound of claim 14 in which $R_p^o$ is allyl.
16. The compound of claim 3 which is 1-allyl-4-hydroxy-2-quinolinone-3-carboxylic acid allyl ester.
17. The compound of claim 15 which is 1-allyl-6,7-dimethoxy-4-hydroxy-2-quinolinone-3-carboxylic acid allyl ester.
18. The compound of claim 8 which is 1-cyclopropylmethyl-6,7-dimethoxy-4-hydroxy-2-quinolinone-3-carboxylic acid allyl ester.
19. The compound of claim 6 which is 1-propargyl-4-hydroxy-2-quinolinone-3-carboxylic acid allyl ester.
20. A compound of claim 14 in which $R_p^o$ is alkyl.
21. The compound of claim 20 which is 1-methyl-6,7-dimethoxy-4-hydroxy-2-quinolinone-3-carboxylic acid allyl ester.
22. A compound of claim 1 in which $R_p$ and $R_p'$ together form 6,7-methylenedioxy.
23. A compound of claim 22 in which $R_p^o$ is alkyl.
24. A compound of claim 22 in which $R_p^o$ is alkenyl.
25. A compound of claim 24 in which $R_p^o$ is allyl.
26. The compound of claim 25 which is 1-allyl-6,7-methylenedioxy-4-hydroxy-2-quinolinone-3-carboxylic acid allyl ester.
27. A compound of claim 14 in which $R_p^o$ is hydrogen.
28. The compound of claim 27 which is 6,7-dimethoxy-4-hydroxy-2-quinolinone-3-carboxylic acid allyl ester.
29. The compound of claim 15 which is 1-allyl-6,7-dimethoxy-4-hydroxy-2-quinolinone-3-carboxylic acid propargyl ester.
30. The method of treating allergic conditions due to histamine release comprising administering to a mammal in need of such treatment an allergy treating effective amount of a compound of claim 1.
31. The method of claim 30 in which $R_p$ and $R_p'$ are independently hydrogen, fluoro, chloro, bromo, alkyl of 1 to 4 carbon atoms, alkoxy of 1 to 4 carbon atoms, nitro or trifluoromethyl.
32. The method of claim 31 in which $R_p^o$ is alkyl.
33. The method of claim 31 in which $R_p^o$ is alkenyl.
34. The method of claim 31 in which $R_p^o$ is hydrogen.
35. The method of claim 31 in which $R_p^o$ is cycloalkyl.
36. The method of claim 31 in which $R_p^o$ is alkynyl.
37. The method of claim 31 in which $R_p^o$ is cycloalkylalkyl.
38. The method of claim 31 in which $R_p^o$ is

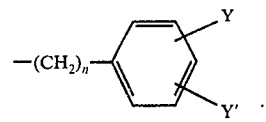

39. The method of claim 38 in which $n$ is 0.
40. The method of claim 38 in which $n$ is 1.
41. The method of claim 30 in which M is hydrogen.
42. The method of claim 31 in which $R_p$ and $R_p'$ are each alkoxy.
43. The method of claim 42 in which $R_p$ and $R_p'$ represent 6,7-dialkoxy.
44. The method of claim 43 in which $R_p$ and $R_p'$ represent 6,7-dimethoxy.
45. The method of claim 33 in which $R_p^o$ is allyl.
46. The method of claim 45 in which $R_p$ and $R_p'$ represent 6,7-dimethoxy.
47. The method of claim 32 in which $R_p$ and $R_p'$ represent 6,7-dimethoxy.
48. The method of claim 34 in which
$R_p$ is hydrogen, fluoro, chloro, bromo, alkyl of 1 to 4 carbon atoms or alkoxy of 1 to 4 carbon atoms and
$R_p'$ is fluoro, chloro, bromo, alkyl of 1 to 4 carbon atoms or alkoxy of 1 to 4 carbon atoms.
49. The method of claim 32 in which $R_p$ and $R_p'$ are independently hydrogen, fluoro, chloro, bromo, alkyl of 1 to 4 carbon atoms or alkoxy of 1 to 4 carbon atoms.
50. The method of claim 48 in which the compound is 6,7-dimethoxy-4-hydroxy-2-quinolinone-3-carboxylic acid allyl ester.
51. The method of claim 49 in which the compound is 1-methyl-4-hydroxy-2-quinolinone-3-carboxylic acid allyl ester.
52. The method of claim 45 in which the compound is 1-allyl-4-hydroxy-2-quinolinone-3-carboxylic acid allyl ester.
53. The method of claim 46 in which the compound is 1-allyl-6,7-dimethoxy-4-hydroxy-2-quinolinone-3-carboxylic acid allyl ester.
54. The method of claim 47 in which the compound is 1-methyl-6,7-dimethoxy-4-hydroxy-2-quinolinone-3-carboxylic acid allyl ester.
55. The method of claim 30 in which $R_p$ and $R_p'$ together form 6,7-methylenedioxy allyl ester.
56. The method of claim 55 in which $R_p^o$ is allyl.
57. The method of claim 56 in which the compound is 1-allyl-6,7-methylenedioxy-4-hydroxy-2-quinolinone-3-carboxylic acid allyl ester.
58. The method of claim 46 in which the compound is 1-allyl-6,7-dimethoxy-4-hydroxy-2-quinolinone-3-carboxylic acid propargyl ester.
59. The method of claim 30 in which the compound is administered at a daily dosage of from 20 to 800 milligrams.
60. The pharmaceutical composition comprising in unit dosage form a pharmaceutically acceptable carrier and an amount effective to relieve allergic conditions due to histamine release of a compound of claim 1.
61. A composition of claim 60 in which $R_p$ and $R_p'$ are independently hydrogen, fluoro, chloro, bromo, alkyl of 1 to 4 carbon atoms, alkoxy of 1 to 4 carbon atoms, nitro or trifluoromethyl.
62. A composition of claim 61 in which $R_p^o$ is alkyl.

63. A composition of claim 61 in which $R_p^o$ is alkenyl.

64. A composition of claim 60 in which M is hydrogen.

65. A composition of claim 60 in which $R_p$ and $R_p'$ are each alkoxy.

66. A composition of claim 65 in which $R_p$ and $R_p'$ represent 6,7-dialkoxy.

67. A composition of claim 66 in which $R_p$ and $R_p'$ represent 6,7-dimethoxy.

68. A composition of claim 63 in which $R_p^o$ is allyl.

69. A composition of claim 68 in which $R_p$ and $R_p'$ represent 6,7-dimethoxy.

70. A composition of claim 62 in which $R_p$ and $R_p'$ represent 6,7-dimethoxy.

71. A composition of claim 68 in which the compound is 1-allyl-4-hydroxy-2-quinolinone-3-carboxylic acid allyl ester.

72. A composition of claim 69 in which the compound is 1-allyl-6,7-dimethoxy-4-hydroxy-2-quinolinone-3-carboxylic acid allyl ester.

73. A composition of claim 70 in which the compound is 1-methyl-6,7-dimethoxy-4-hydroxy-2-quinolinone-3-carboxylic acid allyl ester.

74. A composition of claim 60 in which $R_p$ and $R_p'$ together form 6,7-methylenedioxy.

75. A composition of claim 74 in which the compound is 1-allyl-6,7-methylenedioxy-4-hydroxy-2-quinolinone-3-carboxylic acid allyl ester.

76. A composition of claim 60 containing the compound in an amount of from 5 to 400 milligrams and a solid carrier.

77. A composition of claim 60 in which R is alkenyl.

78. A composition of claim 77 in which R is allyl.

* * * * *